United States Patent
Kaouas et al.

(10) Patent No.: US 11,084,785 B2
(45) Date of Patent: Aug. 10, 2021

(54) ALKENYL CARBONOTHIOATES AS FLAVOUR INGREDIENTS

(71) Applicant: Givaudan SA, Vernier (CH)

(72) Inventors: Abdelmajid Kaouas, Utrecht (NL); Bernard Kranen, Singapore (SG)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 16/605,872

(22) PCT Filed: May 9, 2018

(86) PCT No.: PCT/EP2018/062040
§ 371 (c)(1),
(2) Date: Oct. 17, 2019

(87) PCT Pub. No.: WO2018/206662
PCT Pub. Date: Nov. 15, 2018

(65) Prior Publication Data
US 2021/0122711 A1    Apr. 29, 2021

(30) Foreign Application Priority Data

May 12, 2017    (GB) .................................. 1707639

(51) Int. Cl.
C07C 329/06    (2006.01)
A23L 27/20    (2016.01)
A23F 5/46    (2006.01)

(52) U.S. Cl.
CPC ............ *C07C 329/06* (2013.01); *A23F 5/465* (2013.01); *A23L 27/2022* (2016.08)

(58) Field of Classification Search
CPC ..... C07C 329/06; A23L 27/2022; A23F 5/465
See application file for complete search history.

(56) References Cited

U.S. PATENT DOCUMENTS

| | | |
|---|---|---|
| 3,885,051 A | 5/1975 | Mussinan et al. |
| 3,978,240 A | 8/1976 | Van Der Heijden et al. |
| 6,129,941 A | 10/2000 | Escher et al. |
| 7,585,535 B2 | 9/2009 | Grab et al. |
| 2004/0253362 A1 | 12/2004 | Grab et al. |
| 2008/0260670 A1 | 10/2008 | Natsch et al. |
| 2011/0256071 A1 | 10/2011 | Blandino et al. |
| 2012/0052178 A1 | 3/2012 | Gassenmeier |

FOREIGN PATENT DOCUMENTS

| | | |
|---|---|---|
| EP | 1 170 295 A1 | 1/2002 |
| EP | 1 265 547 A1 | 12/2002 |
| GB | 1379019 A | 1/1975 |
| WO | WO 2007/033508 A2 | 3/2007 |
| WO | WO 2010/042938 A1 | 4/2010 |
| WO | WO 2010/115920 A1 | 10/2010 |

OTHER PUBLICATIONS

Pogulyai, A., et al. Electronic structure of negative monothiocarbonate ions. Russ Chem Bull 36, 2036-2039 (1987) (Year: 1987).*
International Search Report for International Application No. PCT/EP2018/062040, dated Jun. 26, 2018, (7 pages).
Written Opinion for International Application No. PCT/EP2018/062040, dated Jun. 26, 2018 (8 pages).
Faulkner, et al.; "*Application of the Claisen rearrangement to the synthesis of trans trisubstituted olefinic bonds. Synthesis of squalene and insect juvenile hormone.*"; Journal of the American Chemical Society; vol. 95(2), pp. 553-563, Jan. 24, 1973.
Garmaise, et al., "Thino- and thiolcarbonates"; Journal of Organic Chemistry; vol. 27; pp. 4509-4512; 1962.
GB Search Report for Application No. 1707636.5, dated Feb. 22, 2018 (3 pages).
Chem Abstract Accession No. 1973:84574.
Chem Abstract Accession No. 1963:26953.
Sun, et al.; "Current Status and Prospects of Sulfur-containing Flavor Compounds in China"; Beijing Technology and Business University; Beijing, China; pp. 99-102; Dec. 31, 2006.
Xu, et al.; "Progress of Sulfur Spices"; Beijing Technology and Business University; Beijing, China; pp. 5-6; Feb. 28, 2006.

* cited by examiner

*Primary Examiner* — Nikki H. Dees
*Assistant Examiner* — Jeffrey D Benson
(74) *Attorney, Agent, or Firm* — Curatolo Sidoti Co., LPA; Salvatore A. Sidoti; Floyd Trillis, III

(57) ABSTRACT

Provided are new alkenyl carbonothioates of formula (I), their manufacture and their use as flavours and fragrances. Also provided are flavour and fragrance compositions and edible products, in particular coffee products, comprising the new alkenyl carbonothioates.

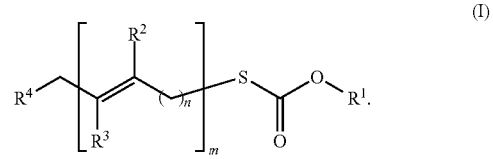

(I)

13 Claims, No Drawings

ALKENYL CARBONOTHIOATES AS FLAVOUR INGREDIENTS

CROSS REFERENCE TO RELATED APPLICATIONS

This application is a national stage application of International Application No. PCT/EP2018/062040, filed 9 May 2018, which claims priority from Great Britain Patent Application No. 1707639.9, filed 12 May 2017, which applications are incorporated herein by reference.

FIELD OF THE INVENTION

The present disclosure relates to use of carbonothioates as flavours and fragrances. More particularly, the present disclosure relates to use of O-alkyl S-hydroxyalkenyl carbonothioates as flavours and fragrances.

BACKGROUND OF THE INVENTION

The flavour and fragrance industry is continuously interested in new ingredients that may enhance, improve or modify the flavour character of consumer products.

The flavour of edible products, such as foodstuffs and beverages consists of two parts: the aroma and the taste. In general, what is provided through the olfactory epithelium in the nasal cavity is referred to as "aroma", whereas the term "taste" is generally used to describe the sensory impact that is perceived via the mouth, especially the tongue.

Surprisingly, inventors have found that the flavour of edible products can be improved significantly by admixing thereto O-alkyl S-hydroxyalkenyl carbonothioates of formula (I) as hereinunder defined.

It has been found that the flavour of a product, compared with a product without a compound of formula (I) as hereinunder defined, was more intense and/or lasted longer. These properties were maintained under processing conditions, such as heating from about 75° C. to about 150° C., which make the compounds of formula (I) particularly suitable for processed foodstuff and beverages, such as instant coffee and powdered coffee beverages.

SUMMARY OF THE INVENTION

In one embodiment, there is provided a compound of formula (I)

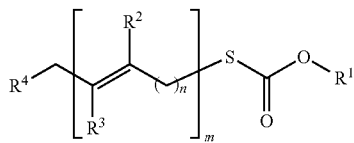

(I)

wherein n is 1 or 2; m is 1, 2 or 3; $R^1$ is alkyl or aryl; and $R^2$, $R^3$, $R^4$ independently represent hydrogen or alkyl.

In another embodiment, a flavour composition includes a compound of formula (I)

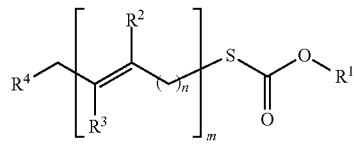

(I)

wherein n is 1 or 2; m is 1, 2 or 3; $R^1$ is alkyl or aryl; and $R^2$, $R^3$, $R^4$ independently represent hydrogen or alkyl; and at least one flavour ingredient.

In yet another embodiment, a beverage product includes a compound selected from the group consisting of O-ethyl S-(3-methylbut-2-en-1-yl) carbonothioate; O-ethyl S-(3-methylbut-3-en-1-yl) carbonothioate; (E)-S-(but-2-en-1-yl) O-ethyl carbonothioate; S-(but-3-en-1-yl) O-ethyl carbonothioate; S-allyl O-ethyl carbonothioate; O-ethyl S-geranyl carbonthioate; O-ethyl S-neryl carbonthioate; and O-ethyl S-farnesyl carbonthioate; a flavour composition; and a product base.

These and other features, aspects and advantages of specific embodiments will become evident to those skilled in the art from a reading of the present disclosure.

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, there is provided a compound of formula (I)

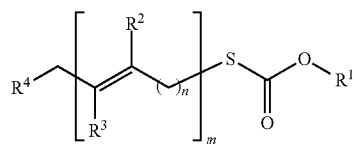

(I)

wherein
n is 1 or 2;
m is 2 or 3;
$R^1$ is alkyl or aryl (e.g. methyl, ethyl, propyl, isobutyl, tea-butyl, phenyl or benzyl); and
$R^2$, $R^3$, $R^4$ independently represent hydrogen or alkyl (e.g. methyl, ethyl or propyl).

The compounds of formula (I) comprise several chiral centers and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, for example, preparative HPLC and GC, crystallization or stereoselective synthesis.
In particular embodiments compounds of formula (I) are selected from
O-ethyl S-(3-methylbut-2-en-1-yl) carbonothioate;
O-ethyl S-(3-methylbut-3-en-1-yl) carbonothioate;
(E)-S-(but-2-en-1-yl) O-ethyl carbonothioate;
S-(but-3-en-1-yl) O-ethyl carbonothioate;
S-allyl O-ethyl carbonothioate;
O-ethyl S-geranyl carbonothioate;
O-ethyl S-neryl carbonthioate; and
O-ethyl S-farnesyl carbonthioate.

The compounds of formula (I) may be used alone or in combination with other substances useful for the required purpose, for example, fragrances or flavours. In one embodiment, the compounds of formula (I) may be combined with other flavours and/or fragrances selected from the extensive range of natural and synthetic molecules currently available, such as ethereal oils and extracts, alcohols, aldehydes and ketones, ethers and acetals, esters and lactones, macrocycles and heterocycles.

Accordingly, there is provided in a further embodiment a flavour composition comprising a compound of formula (I) and at least one further flavour ingredient.

In another embodiment, the compounds of formula (I) may be admixed with one or more ingredients or excipients conventionally used in conjunction with flavours or fragrances in fragranced/flavoured applications, for example, carrier materials, and other auxiliary agents, such as solvents (for example, dipropyleneglycol (DPG), isopropylmyristate (IPM), triethylcitrate (TEC), ethanol, propylene glycol (PG), triacetine, and benzylic alcohol), commonly used in the art. The compounds of formula (I) may be dissolved or dispersed in a carrier material, such as a fat, or enrobed with maltose-dextrin, gelatine, gum Arabic and the like. They may be mixed with the food ingredients ready to be prepared or mixed with one of the ingredients.

In a further embodiment there is provided a flavour application comprising a compound of formula (I) and a product base.

Flavoured applications for which the compounds of formula (I) are particularly suitable are foodstuffs and beverages such as dry, canned, frozen and instant soups, ready meals, croquettes, sauce cubes, bouillon cubes, baking fats, margarine, bread, cakes, and instant drinks which are prepared with hot water, such as instant coffee and powdered coffee beverages, beer, soft drinks, flavoured tea and dairy products. This list of products is given by way of illustration and is not to be regarded as being in any way limiting.

As used herein, by "product base" in conjunction with flavour applications is meant an edible product, not containing a compound of formula (I) as hereinabove defined.

As used herein, by "edible products" are meant products such as foodstuffs and beverages, or personal care products that are intended to be introduced into the oral cavity of a human or animal and remain there for a certain period of time before being ingested or removed from the mouth. Such products include compositions in their processed, partially processed or unprocessed state.

The compound of formula (I) may be present in applications in amounts ranging from about 0.001 ppb to about 1.0 ppb, in another embodiment from about 0.002 ppb to about 0.5 ppb, in yet another embodiment from about 0.003 ppb to about 0.3 ppb, by weight of the application.

If used in flavour compositions, the compound of formula (I) may be present in amounts ranging from about 0.005 ppm to about 5.0 ppm, in another embodiment from about 0.01 ppm to about 1.0 ppm, based on the flavour composition.

In another embodiment, the compound of formula (I) may be used in a broad range of fragrance applications, for example, in any field of fine and functional perfumery, such as perfumes, household products, laundry products, body care products and cosmetics.

If used in fragrance applications, the compound of formula (I) may be present in amounts ranging from about 1-30 ppm based on the fragrance application. However, these values are given only by way of example, since the experienced perfumer may also achieve effects or may create novel accord with lower or higher concentrations.

The compounds of formula (I) may be employed into a product base by mixing the compound, or a fragrance/flavour composition comprising it, with the product base, and/or they may, in an earlier step, be entrapped with an entrapment material, and then mixed with the consumer product base.

The compounds of formula (I) may be prepared as depicted in scheme 1 under conditions known to the skilled person. Further particulars as to reaction conditions are provided in the examples.

Scheme 1

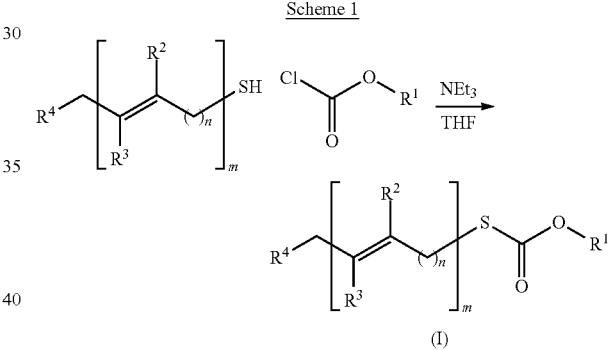

n; m; R1; R2; R3 and R4 have the same meaning as given for formula (I) above.

In one embodiment, O-ethyl S-(3-methylbut-2-en-1-yl) carbonothioate may be prepared as follows:

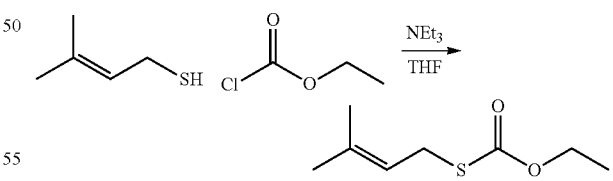

When n and m are 1; $R^1$ is ethyl; $R^2$ is hydrogen; R3 is methyl and R4 is hydrogen.

In another embodiment, O-ethyl S-geranyl carbonthioate may be prepared as follows:

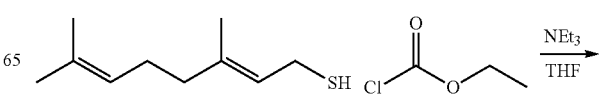

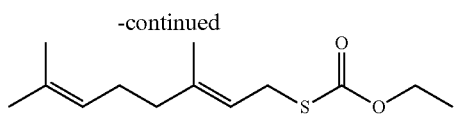

When n is 1; m is 2; R1 is ethyl; R2 is hydrogen; R3 is methyl and R4 is hydrogen.

In another embodiment, O-ethyl S-farnesyl carbonthioate may be prepared as follows:

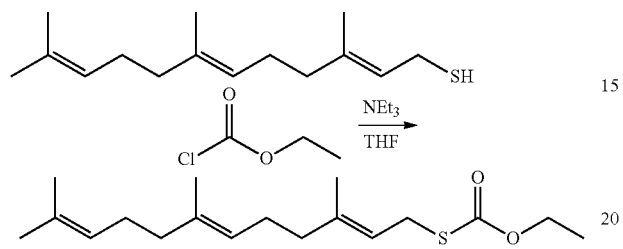

When n is 1; m is 3; R1 is ethyl; R2 is hydrogen; R3 is methyl and R4 is hydrogen.

EXAMPLES

The following examples are given solely for the purpose of illustration and are not to be construed as limitations of the present invention, as many variations of the invention are possible without departing from the spirit and scope of the present disclosure. Using a bench-top tasting panel (consisting of 6 panelists), panelists were asked to record the flavour and odor characteristics of the example samples.

Example 1

O-ethyl S-(3-methylbut-2-en-1-yl) carbonothioate

Under nitrogen, ethyl chloroformate (323 mmol) was added dropwise to a solution of prenylmercaptan (294 mmol) and triethylamine (323 mmol) in 400 ml of anhydrous THF in an ice/acetone bath (−1° C.). After the dosing, the cooling bath was removed and stirring was continued for 1 hour. It was worked-up by filtration and the filtrate was concentrated under vacuum. The residue was dissolved in diethyl ether and washed accordingly with aqueous HCl, aqueous sodium carbonate and water. The organic phase was dried on magnesium sulfate and purified by distillation giving 33.8 gram of the product (66% yield).

Flavour description: sulfury, blackcurrant, tropical, roasted coffee.

Odor description: mushroom, herbaceous, slightly cocoa connotation.

Example 2

Black Coffee

Black coffee was prepared from the following ingredients:

| 13 g roasted coffee bean (50% Brazil, 50% Colombia) extracted with 350 ml hot water | |
| --- | --- |
| Sodium bicarbonate | 0.7 g |
| Distilled water | ad 1000 g |

To a portion of the black coffee was added 0.003 ppb of O-ethyl S-(3-methylbut-2-en-1-yl) carbonothioate, relative to the weight of the coffee. The coffee was packed in cans and retorted at 121° C. for 10 minutes. The black coffee possessed a reduced off-note (acidity), dark chocolate and smooth taste.

To another portion of the black coffee was added 0.03 ppb of O-ethyl S-(3-methylbut-2-en-1-yl) carbonothioate, relative to the weight of the coffee. The coffee was packed in cans and retorted at 121° C. for 10 minutes. The black coffee possessed a rich taste, good top note and smooth taste.

To yet another portion of the black coffee was added 0.3 ppb of O-ethyl S-(3-methylbut-2-en-1-yl) carbonothioate, relative to the weight of the coffee. The coffee was packed in cans and retorted at (21° C. for 10 minutes. The black coffee possessed a slightly metallic, burnt, animal-like taste.

Example 3

Regular Coffee

Regular coffee was prepared from the following ingredients:

| 13 g roasted coffee bean (50% Brazil, 50% Colombia) extracted with 350 ml hot water | |
| --- | --- |
| Whole Milk | 130 g |
| Granulated Sugar | 54 g |
| Emulsifier | 1.35 g |
| Casein Sodium | 1.0 g |
| Sodium bicarbonate | 1.3 g |
| Distilled water | ad 1000 g |

The regular coffee (Control) was packed in cans and retorted at 124° C. for 20 minutes. The regular coffee (Control) was described as less dark roast, flat, less fresh.

To a portion of the regular coffee was added 0.03 ppb of O-ethyl S-(3-methylbut-2-en-1-yl) carbonothioate, relative to the weight of the coffee. The coffee was packed in cans and retorted at 124° C. for 20 minutes. The regular coffee possessed a cigar-like, burnt sugar, slightly good smoky, roundness, masking off-note (milk).

To another portion of the regular coffee was added 0.3 ppb of O-ethyl S-(3-methylbut-2-en-1-yl) carbonothioate, relative to the weight of the coffee. The coffee was packed in cans and retorted at 124° C. for 20 minutes. The regular coffee possessed a boost, good body, slightly (negative) burnt taste.

To yet another portion of the regular coffee was added 3 ppb of O-ethyl S-(3-methylbut-2-en-1-yl) carbonothioate, relative to the weight of the coffee. The coffee was packed in cans and retorted at 124° C. for 20 minutes. The regular coffee possessed a strong, metallic, animal-like, burnt, bitter taste.

Example 4

Café au Lait

Café au Lait was prepared from the following ingredients:

| 10 g roasted coffee bean (50% Brazil, 50% Colombia) extracted with 350 ml hot water | |
| --- | --- |
| Whole Milk | 220 g |
| Granulated Sugar | 50 g |

| | |
|---|---|
| 10 g roasted coffee bean (50% Brazil, 50% Colombia) extracted with 350 ml hot water | |
| Emulsifier | 1.35 g |
| Casein Sodium | 1.0 g |
| Sodium bicarbonate | 1.0 g |
| Distilled water | ad 1000 g |

The Café au Lait (Control) was packed in cans and retorted at 124° C. for 20 minutes. The Café au Lait (Control) was described as less roast, flat, less fresh, with the cooked milk note coming through.

To a portion of the Café au Lait was added 0.03 ppb of O-ethyl S-(3-methylbut-2-en-1-yl) carbonothioate, relative to the weight of the coffee. The Café au Lait was packed in cans and retorted at 124° C. for 20 minutes. The Café au Lait possessed a sweet, milky, mild roast note with good roundness and had clearly improved roast notes over the Control.

To another portion of the Café au Lait was added 0.3 ppb of O-ethyl S-(3-methylbut-2-en-1-yl) carbonothioate, relative to the weight of the coffee. The Café au Lait was packed in cans and retorted at 124° C. for 20 minutes. The Café au Lait possessed a nice balance, smooth, deeply good roundness.

To yet another portion of the Café au Lait was added 3 ppb of O-ethyl S-(3-methylbut-2-en-1-yl) carbonothioate, relative to the weight of the coffee. The Café au Lait was packed in cans and retorted at 124° C. for 20 minutes. The Café au Lait possessed an unbalanced, metallic, sulphury and skunky note.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound selected from the group consisting of O-ethyl S-(3-methylbut-2-en-1-yl) carbonothioate; O-ethyl S-(3-methylbut-3-en-1-yl) carbonothioate; (E)-S-(but-2-en-1-yl) O-ethyl carbonothioate; S-(but-3-en-1-yl) O-ethyl carbonothioate; O-ethyl S-geranyl carbonothioate; O-ethyl S-neryl carbonothioate; O-ethyl S-farnesyl carbonothioate; and mixtures thereof.

2. An edible product including the compound according to claim 1 admixed thereto.

3. A flavour composition comprising a compound selected from the group consisting of O-ethyl S-(3-methylbut-2-en-1-yl) carbonothioate; O-ethyl S-(3-methylbut-3-en-1-yl) carbonothioate; (E)-S-(but-2-en-1-yl) O-ethyl carbonothioate; S-(but-3-en-1-yl) O-ethyl carbonothioate; O-ethyl S-geranyl carbonothioate; O-ethyl S-neryl carbonothioate; O-ethyl S-farnesyl carbonothioate; and mixtures thereof.

4. The flavour composition according to claim 3, wherein the compound is present at a level of from about 0.005 ppm to about 5.0 ppm by weight of the flavour composition.

5. The flavour composition according to claim 3, wherein the compound is present at a level of from about 0.01 ppm to about 1.0 ppm by weight of the flavour composition.

6. The flavour composition according to claim 3, further comprising a carrier material.

7. A beverage product comprising:
a compound selected from the group consisting of O-ethyl S-(3-methylbut-2-en-1-yl) carbonothioate; O-ethyl S-(3-methylbut-3-en-1-yl) carbonothioate; (E)-S-(but-2-en-1-yl) O-ethyl carbonothioate; S-(but-3-en-1-yl) O-ethyl carbonothioate; O-ethyl S-geranyl carbonothioate; O-ethyl S-neryl carbonothioate; O-ethyl S-farnesyl carbonothioate; and mixtures thereof;
a flavour composition; and
a product base.

8. The beverage product according to claim 7, wherein the compound is present at a level of from about 0.001 ppb to about 1.0 ppb by weight of the beverage product.

9. The beverage product according to claim 7, wherein the compound is present at a level of from about 0.002 ppb to about 0.5 ppb by weight of the beverage product.

10. The beverage product according to claim 7, wherein the compound is present at a level of from about 0.003 ppb to about 0.3 ppb by weight of the beverage product.

11. The beverage product according to claim 7, wherein the flavour composition includes at least one flavour ingredient.

12. The beverage product according to claim 7, wherein the flavour composition includes a carrier material.

13. The beverage product according to claim 7, wherein the beverage product is coffee.

* * * * *